US011382752B2

(12) United States Patent
McGuckin, Jr.

(10) Patent No.: US 11,382,752 B2
(45) Date of Patent: Jul. 12, 2022

(54) MINNIMALLY INVASIVE DEVICE FOR TREATING CHRONIC HEART FAILURE (71) Applicant: Rex Medical, L.P., Conshohocken, PA (US)

(72) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 67 days.

(21) Appl. No.: 16/727,044

(22) Filed: Dec. 26, 2019

(65) Prior Publication Data
US 2020/0229927 A1 Jul. 23, 2020

Related U.S. Application Data (60) Provisional application No. 62/794,538, filed on Jan. 18, 2019.

(51) Int. Cl.
*A61F 2/24* (2006.01)

(52) U.S. Cl.
CPC .... *A61F 2/2481* (2013.01); *A61F 2002/2484* (2013.01)

(58) Field of Classification Search
CPC ............ A61F 2002/2484; A61F 2/2481; A61F 2220/0016; A61F 2/2487; A61B 17/0057; A61B 2017/00243; A61B 2017/00575; A61B 2017/00579
See application file for complete search history.

(56) References Cited

U.S. PATENT DOCUMENTS

| | | | |
|---|---|---|---|
| 2006/0025800 A1* | 2/2006 | Suresh | A61B 17/0057 606/198 |
| 2010/0152523 A1* | 6/2010 | MacDonald | A61M 60/148 600/16 |
| 2016/0144074 A1* | 5/2016 | Matheny | A61F 2/2481 424/423 |

* cited by examiner

*Primary Examiner* — Christine H Matthews
(74) *Attorney, Agent, or Firm* — Neil D. Gershon (57) ABSTRACT

A device for treating chronic heart failure made of a construct composed of cardiac tissue and a frame supporting the construct. The frame has a plurality of elongated members and the cardiac tissue is attached to the elongated members. The elongated members extend outwardly from a converging region and diverge to provide a distal opening and a space proximal of the distal opening between the elongated members, the space dimensioned to fit over a heart of the patient to treat chronic heart failure.

10 Claims, 9 Drawing Sheets

MINNIMALLY INVASIVE DEVICE FOR TREATING CHRONIC HEART FAILURE

This application claims priority from provisional application Ser. No. 62/794,538, filed Jan. 18, 2019, the entire contents of which are incorporated herein by reference.

BACKGROUND OF THE INVENTION

1. Field of the Invention

This application relates to a device and method for treating chronic heart failure, and, more particularly, to a device insertable minimally invasively to extend around the heart to treat chronic heart failure.

2. Background of the Related Art

The need exists for devices and method for treating chronic heart failure (CHF). Recent attempts to treat CHF are disclosed in Patent Publications 2016/0253084 and 2018/0223259. According to these patent publications, the incidence of heart failure is over 550,000 each year, and results in more deaths than cancer, accidents and strokes combined. According to these publications, the approach of treating CHF by injecting stem cells and/or progenitor cells directly into the heart using different cell types has had limited success.

These publications discuss a different approach to treating CHF. These publications disclose a method for preparing a contractile construct by 1) seeding immature contractile cells onto the surface of a three dimensional fibroblast containing scaffold (3DFCS) to produce a contractile construct; and 2) culturing the construct to promote differentiation of the immature contractile cells into mature contractile cells, wherein the mature contractile cells form striations. Thus, according to these disclosures, the contractile cells are adhered to the surface of the 3DFCS wherein the construct is capable of spontaneous synchronized contractions across the surface of the 3DFCS with the three dimensional structure having interstitial spaces bridged by the cells in the construct with the cells attaching to the three dimensional framework. Examples of the 3DFCS disclosed include a patch or a woven mesh. The contractile cells can include for example cardiomyocytes, smooth muscles cells, skeletal muscle cells or combinations thereof. The publications disclose attaching the construct to the epicardium and the three dimensional support framework allows cells to attach to it and allows cells to grow into more than one layer. As stated, the methods utilize 3DFCS as a delivery system for cell-based therapy using the heart as its own bioreactor to support the engraftment/growth of cells seeded on the 3DFCS.

The publications state generally there are various ways of implantation (open cavity, minimally invasive, robotically, catheter) and describe various ways of attachment of one or more of the constructs with the heart—glue, adhesive, laser dye, polarization hydrogel, and suturing. Uses to treat other heart conditions such as cardiac arrest, congestive heart failure, coronary heart disease among many others are listed in the publications to treat disorders that can benefit from enhancing, repairing or restoring skeletal or muscle tissue.

Although these two publications disclose a device for treating heart failure, they do not disclose an effective minimally invasive way to insert, position and retain the constructs. Achieving such implantation in a minimally invasive fashion is a difficult task due to the complexities of heart surgery. However, it would be quite advantageous to provide a device to deliver such contractile cells for treating heart conditions in a less invasive fashion. Such minimally invasive procedures as compared to open procedures would open the procedure to more of the elderly patient population which might not be able to withstand open procedures. It would also facilitate the procedure and greatly reduce recovery time, hospital stay periods and costs as well as reduce the risk of infection.

SUMMARY

The present invention advantageously provides a minimally invasive device for delivering and retaining contractile cells to the heart for treating chronic heart failure or other heart disorders/conditions. By such minimally invasive insertion, hospital time and recovery time are greatly reduced and the treatment can be more widely available to a population where open procedures are not indicated.

The device in one aspect includes a support frame for carrying the membrane of cardiac tissue. The support frame is collapsible for insertion and then expands for circumferential placement around the heart.

In one aspect, the present invention provides a device for treating chronic heart failure comprising a construct composed of tissue, e.g. cardiac tissue, and a frame supporting the construct. The frame comprises a plurality of elongated members and the construct is attached to the elongated members. The elongated members extend outwardly from a converging region and diverge to provide a distal opening and a space proximal of the distal opening between the elongated members, the space dimensioned to fit over a heart of the patient to treat chronic heart failure.

In some embodiments, the frame is composed of shape memory metal. In some embodiments, the frame has a plurality of tines which engage cardiac tissue to retain the frame around the heart.

In some embodiments, the frame is composed of a plurality of wires; in other embodiments, the frame is composed of a plurality of struts.

The converging region can in some embodiments include a connection structure for releasable connection to a delivery member. In some embodiments, the connection structure comprises a threaded engagement with the delivery member.

In some embodiments, the frame is movable from a first non-expanded position for delivery in a space between the vertebrae and a second expanded position for placement around the heart. In some embodiments, the device automatically moves to the second expanded position when exposed from the delivery system.

The elongated members in some embodiments terminate in blunt atraumatic ends.

In accordance with another aspect of the present invention, a system for treating chronic heart failure of a patient is provided comprising a delivery system and a device configured for positioning circumferentially around a heart of the patient. The device is composed of a frame and a construct made of cardiac tissue connected to the frame, the frame movable between a first position within a delivery member of the delivery system and a second expanded position when exposed from the delivery member. The delivery system further includes an elongated delivery element detachably connected to the frame and positioned within the delivery member.

In some embodiments, the delivery member is positioned in the intercostal space for minimally invasive insertion of the device.

In some embodiments, the frame comprises a plurality of elongated members diverging from a proximal region to provide an open space dimensioned to fit over the heart of the patient.

In some embodiments, the delivery element is rotatable to detach the delivery element from the frame.

In some embodiments, the frame has a plurality of penetrating members extending therefrom which engage cardiac tissue to retain the frame around the heart.

In accordance with another aspect of the present invention, a method for minimally invasively treating chronic heart failure is provided comprising:

providing a device having a frame and cardiac tissue attached to the frame;
inserting the device through a delivery member extending through the intercostal space of a patient;
exposing the device from the delivery member so the device expands; and
placing the device around the heart to treat chronic heart failure.

In some embodiments, the frame has a plurality of tines which engage the heart to retain the device around the heart.

In some embodiments, the device is inserted minimally invasively between the thoracic vertebrae. In some embodiments, the device is inserted between the T4 and T5 vertebrae.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein.

DETAILED DESCRIPTION OF PREFERRED EMBODIMENTS

The present invention comprises a support frame to support and deliver a contractile construct comprising contractile cells. The contractile construct includes a three dimensional fibroblast containing scaffold with contractile cells adhered to the surface. The contractile construct can be prepared in accordance with the disclosure of U.S. Patent Publications 2016/0253084 (also referred to herein as the '084 publication) and 2018/0223259 (also referred to herein as the '259 publication), i.e., 1) seeding immature contractile cells onto the surface of a three dimensional fibroblast containing scaffold (3DFCS) to produce a contractile construct; and 2) culturing the construct to promote differentiation of the immature contractile cells into mature contractile cells, wherein the mature contractile cells form striations. The contractile cells are adhered to the surface of the 3DFCS wherein the construct is capable of spontaneous synchronized contractions across the surface of the 3DFCS with the three dimensional structure having interstitial spaces bridged by the cells in the construct with the cells attaching to the three dimensional framework. The 3DFCS can be in the form of a patch, a woven mesh or other construct. As disclosed in the '084 and '259 publications, the contractile cells can include for example cardiomyocytes, smooth muscles cells, skeletal muscle cells or combinations thereof.

The construct is supported by the support frame of the present invention and delivered to the heart via the support frame. In this manner, the frame enables minimally invasive delivery of the construct and improved adherence to cardiac tissue as the frame is positioned around the heart as discussed in detail below, and in some embodiments secured to the cardiac tissue via retention members.

The '084 and '259 publications disclose attaching the construct to the epicardium. The three dimensional support framework allows cells to attach to it and allows cells to grow into more than one layer. As stated, the methods utilize 3DFC as a delivery system for cell-based therapy using the heart as its own bioreactor to support the engraftment/growth of cells seeded on the 3DFC.

Figure 1A:
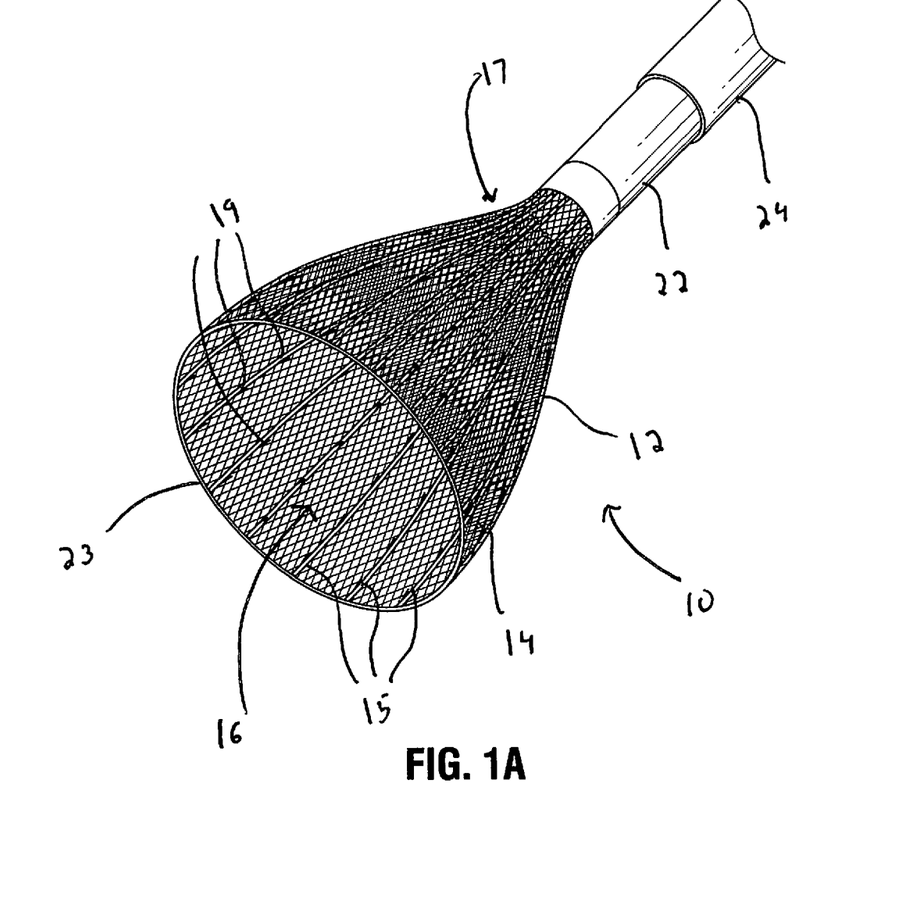
FIG. 1A is a perspective view of a first embodiment of the device of the present invention shown in the expanded position.

Referring now to the drawings wherein like reference numerals identify similar structural features of the device disclosed herein, there is illustrated in FIG. 1A a first embodiment of the device of the present invention designated generally by reference numeral 10. Device 10 includes a support frame 12 and a construct 14 containing a three dimensional construct such as a patch, fabric or mesh containing contractile cells adhered thereto. The construct can be that of the construct disclosed in the '084 and '259 publications. The device of the present invention provides a carrier, a deliverer and cardiac placement supporter for such construct.

Figure 1B:
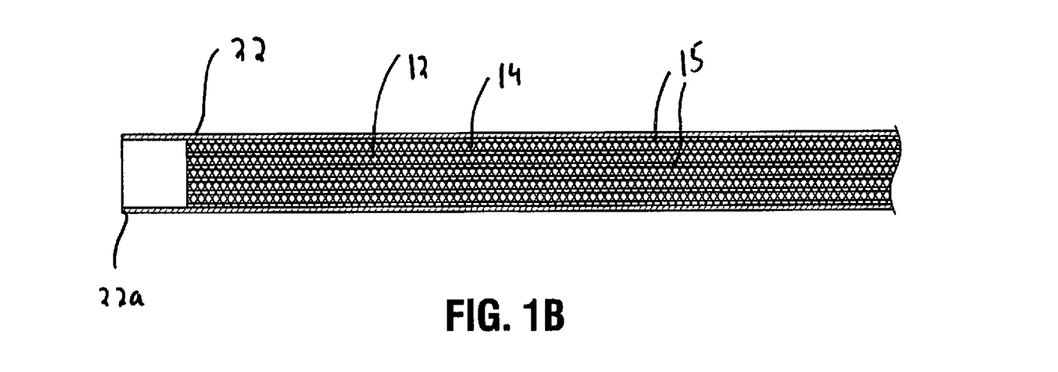
FIG. 1B is a side view of the device of FIG. 1A in a collapsed position within an insertion tube.
Figure 1C:
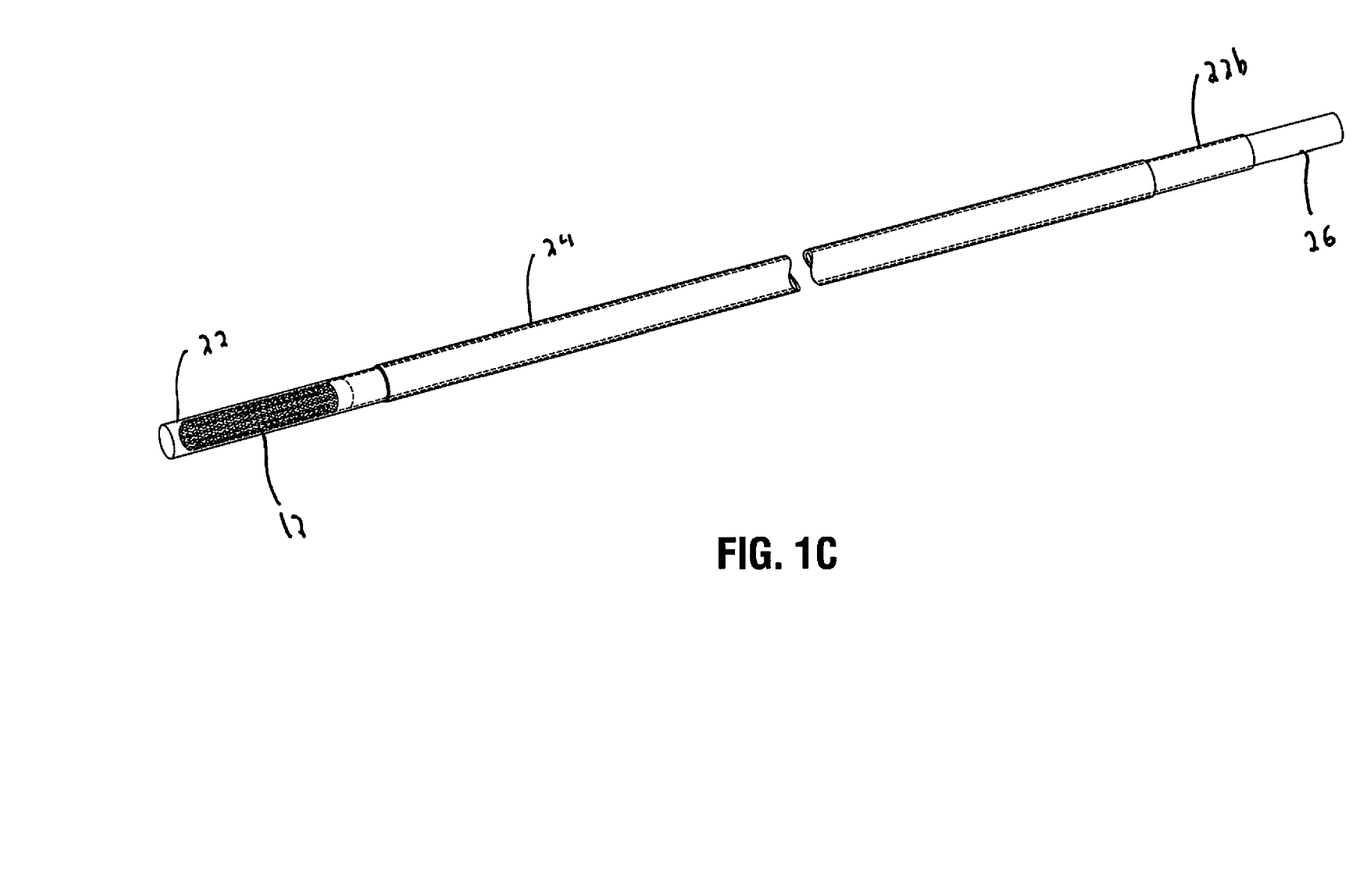
FIG. 1C is a perspective view of the device in a collapsed position within the insertion tube.
Figure 2:
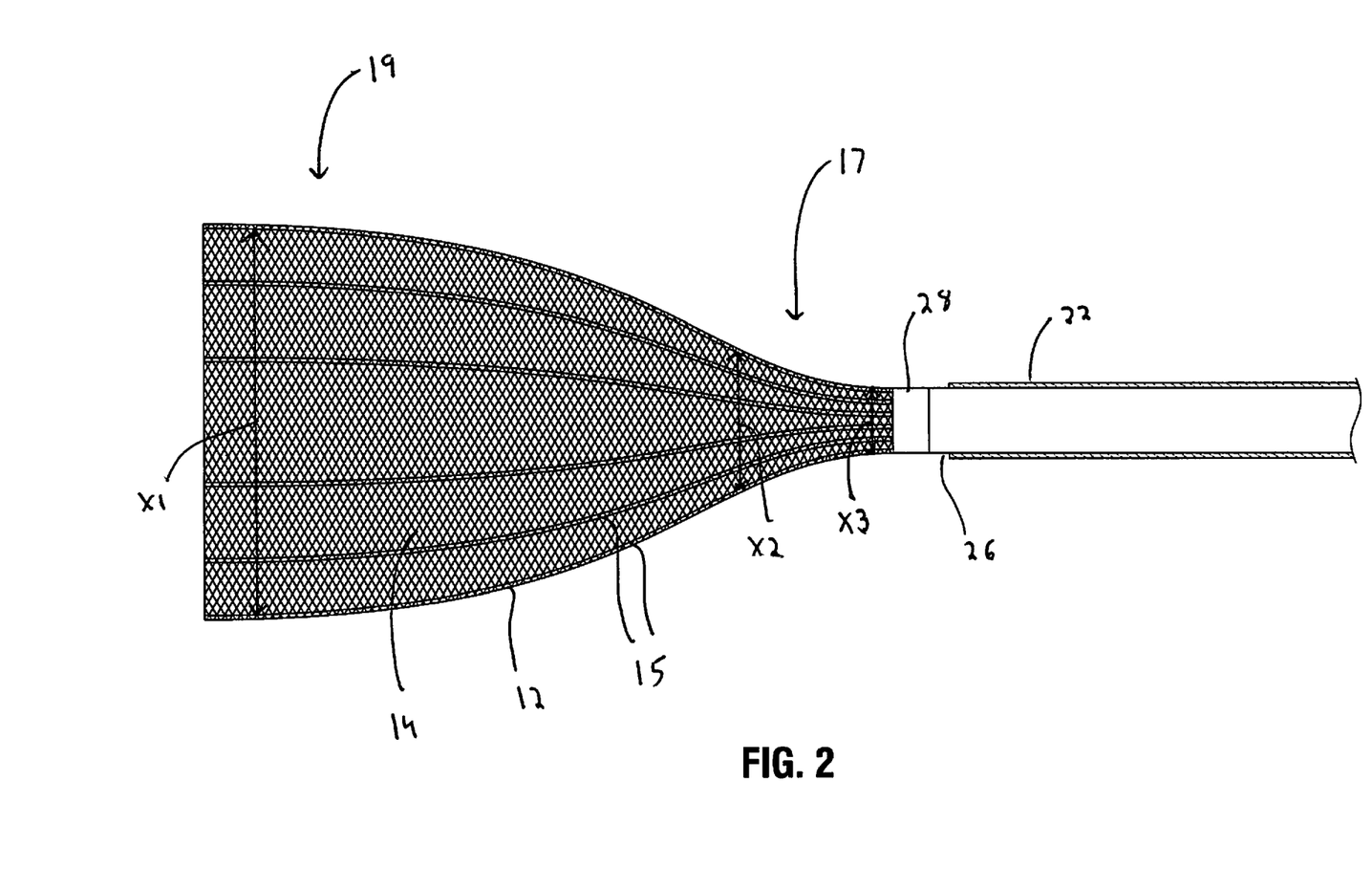
FIG. 2 is a side view of the device of FIG. 1A shown in the expanded position extending from the insertion tube.
Figure 3:
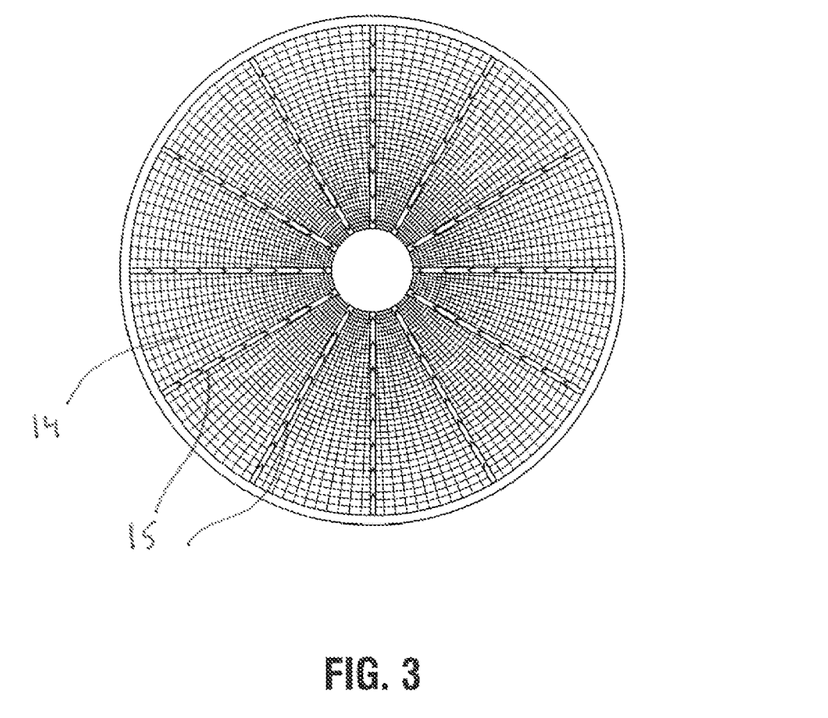
FIG. 3 is a front view of the device of FIG. 2.

The frame 12 is movable from a reduced profile or collapsed position as shown in FIG. 1B to a greater profile or expanded position as shown in FIG. 1A. In the expanded position, the frame 12 has a widened opening 16 at a distal end dimensioned to fit over a heart of the patient. The frame 12 is configured and dimensioned to open to a sufficient size to encapsulate or surround the heart (either partially or preferably fully) so the membrane of cardiac tissue 14 (the construct) carried (supported) by the frame 12 can encapsulate the heart as described in detail below in conjunction with the method of use. The frame 12 comprises a plurality of elongated members 15 and the construct 14 is attached to the elongated members 15. The elongated members 15 extend outwardly from a converging region 17 and diverge to provide a distal opening 16 and a space proximal of the distal opening 16 between the elongated members 15, the space dimensioned to fit over a heart of the patient to treat chronic heart failure. The elongated members in some embodiments terminate in blunt atraumatic free ends to provide more flexibility as in FIG. 2; in other embodiments such as illustrated in FIG. 1A they are connected at their terminal ends by a ring or circular support 23.

The elongated members 15 forming frame 12 can be in the form of a plurality of struts 15. In some embodiments, the struts 15 can be formed from a laser cut tube. Alternatively, the elongated members 15 of the frame 12 can be formed by a plurality of wires or other structure. The struts or wires have sufficient strength to support and maintain the construct in the open position. The struts and wires can have sufficient flexibility to conform to the shape of the heart so the opening and elongated member would further expand as the device is advanced over the heart and placed circumferentially thereover.

The elongated members 15 can be made of shape memory material such as Nitinol, with a shape memorized open position of FIG. 1A. The struts 15 are maintained in a collapsed (non-expanded) position within an insertion sheath 22. When the frame 12 is exposed from the insertion sheath 22, by advancement of the delivery tube 26 and/or retraction of the insertion sheath 22, the elongated members 15 are no longer confined by the wall of the delivery tube 26 and can expand to their open position of FIG. 1A.

In the open position, the frame 12 has a first transverse dimension, e.g., diameter, X1 at a distal region 22 larger than the transverse dimension, e.g., diameter, X3 at a proximal region (at the converging end). The transition from the larger to the smaller dimension is shown in region 17 with a transverse dimension, e.g., diameter, X2 representative of the transverse dimension smaller than the transverse dimension X1 at the distal region and greater than the transverse dimension X3 at the proximal region.

In some embodiments, a plurality of retention members, e.g., tines or barbs 19, extend from the struts 15 and are preferably configured with penetrating tips to penetrate cardiac tissue to maintain the frame 12 in position. The retention members 19 are shown axially spaced along the elongated members 15. The retention members 19 are shown in FIG. 1A as provided one each of the elongated members 15, however, it is also contemplated that the retention members 19 could be provided on only some of the elongated members 15. Also, the number of retention members 19 can be fewer or greater than the number shown in FIG. 1A, and the spacing of the retention members 19 can be different than that shown in FIG. 1A. Other ways of securement to cardiac tissue are also contemplated.

Figure 4:
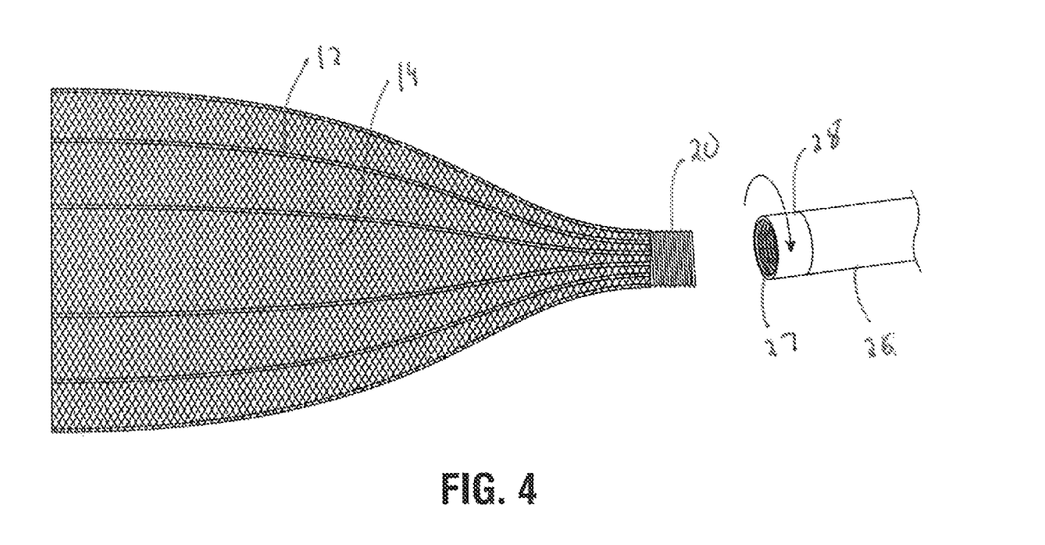
FIG. 4 is a side view of the device being detached (unscrewed) from the delivery tube.

The converging end can in some embodiments include a connection structure for releasable connection to a delivery member. The device 10 is attached to a delivery tube 26 for insertion into the body and adjacent the heart. One method of attachment and detachment is the threaded engagement shown in FIG. 4 wherein the device 10 has a threaded tube 20 at a proximal portion extending proximally from the converging region 17. Delivery tube 26 has a tubular portion 28 at a distal end with a threaded region 27 to threadedly engage the threads of tube 22 of device 10. Note that in FIG. 4, the device 10 has external threads and the delivery tube 26 has internal threads, however, it is also contemplated that the tube 20 of device 10 has the internal threads and the delivery tube 26 has external threads so the delivery tube end would fit inside the tubular portion (tube 20) of the device 10. In either method, the threaded engagement enables the device 10 to be carried (supported) by the delivery tube 26 for passage through the insertion sheath 22 and placement over the heart. Once the device 10 is placed over the heart, the delivery tube 26 is rotated to unscrew the device 10 to detach the delivery tube 26 from the device 10 to leave the device 10 within the patient's body encapsulating the heart.

It should be appreciated that the screw thread is provided as one example of attachment/detachment of the device to/from the delivery tube as other methods of attachment are also contemplated such as a snap fit, bayonet mount, release latch, etc.

The method of use of the device will now be described in conjunction with FIGS. 5-9 which show the steps for delivering the device 10 to the heart. The method provides percutaneous or minimally invasively treatment of chronic heart failure which results in the advantages of minimally invasive surgery described above.

Figure 5:
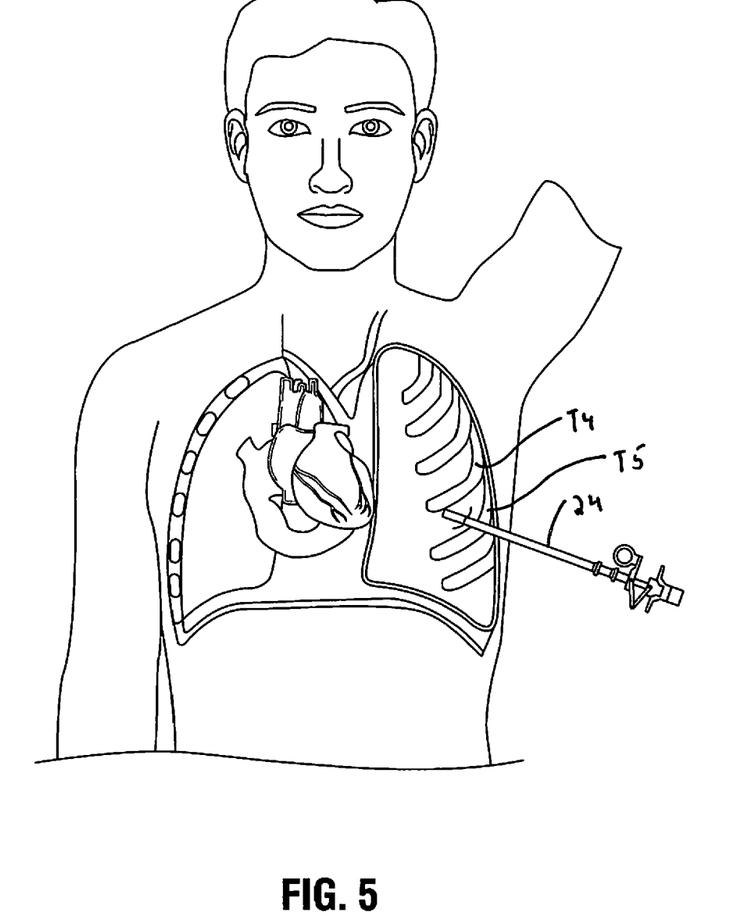
FIG. 5 illustrates an access sheath inserted between the 4$^{th}$ and 5$^{th}$ thoracic vertebrae (T4, T5) to access the heart.
Figure 6:
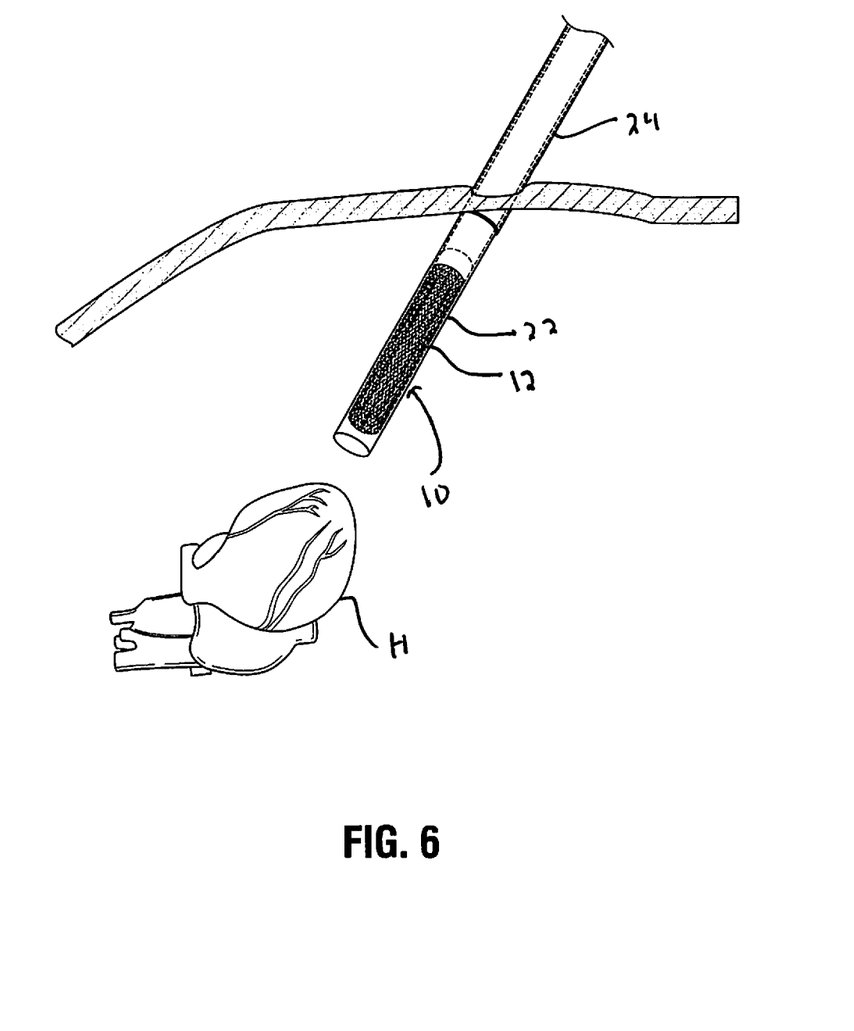
FIG. 6 illustrates the insertion tube inserted through and extending distally of the access sheath for positioning adjacent the heart.
Figure 7:
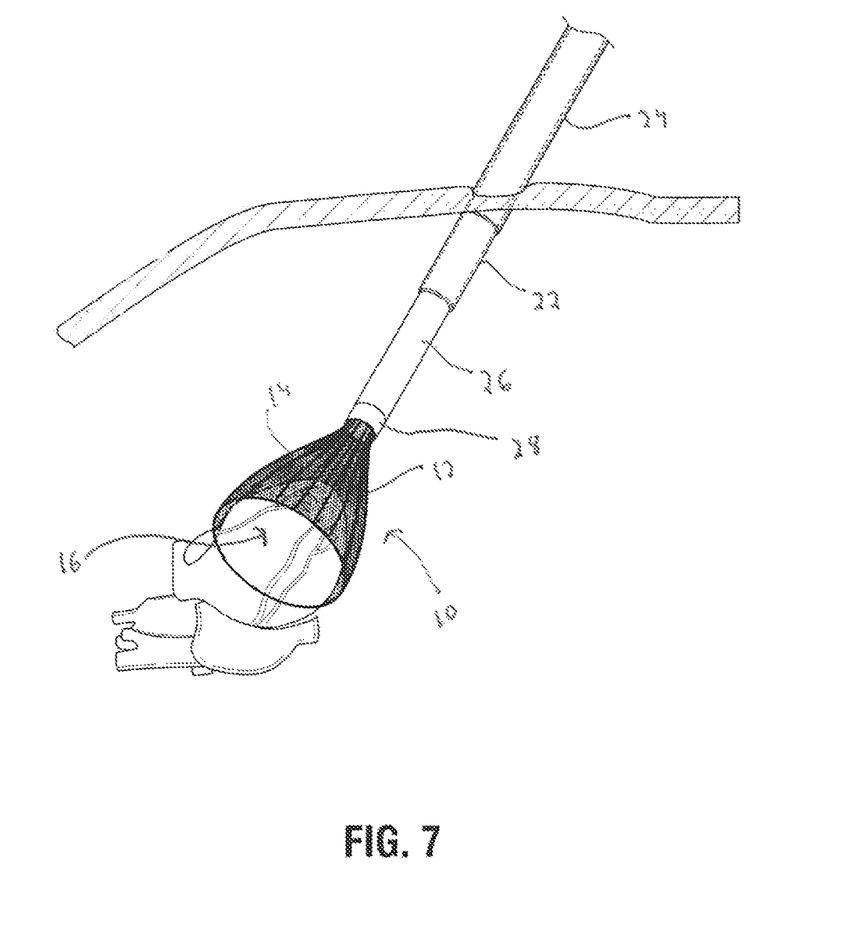
FIG. 7 illustrates the device of FIG. 1A being advanced by the delivery tube to encircle the heart of the patient.
Figure 8:
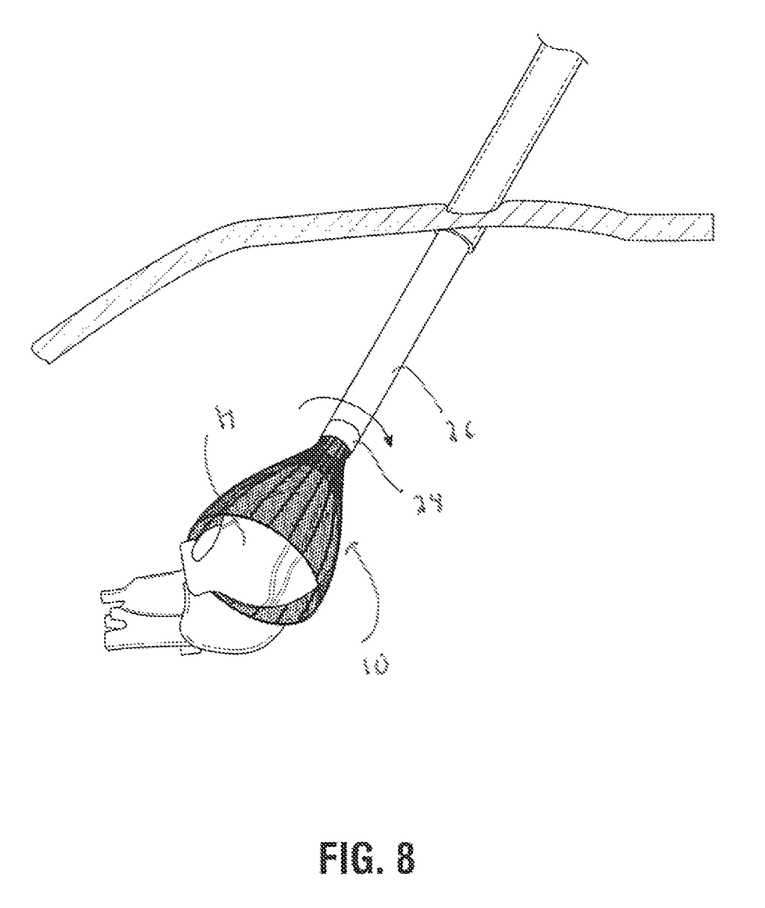
FIG. 8 illustrates the device of FIG. 1A positioned over the heart of the patient and the delivery tube being rotated for detachment.
Figure 9:
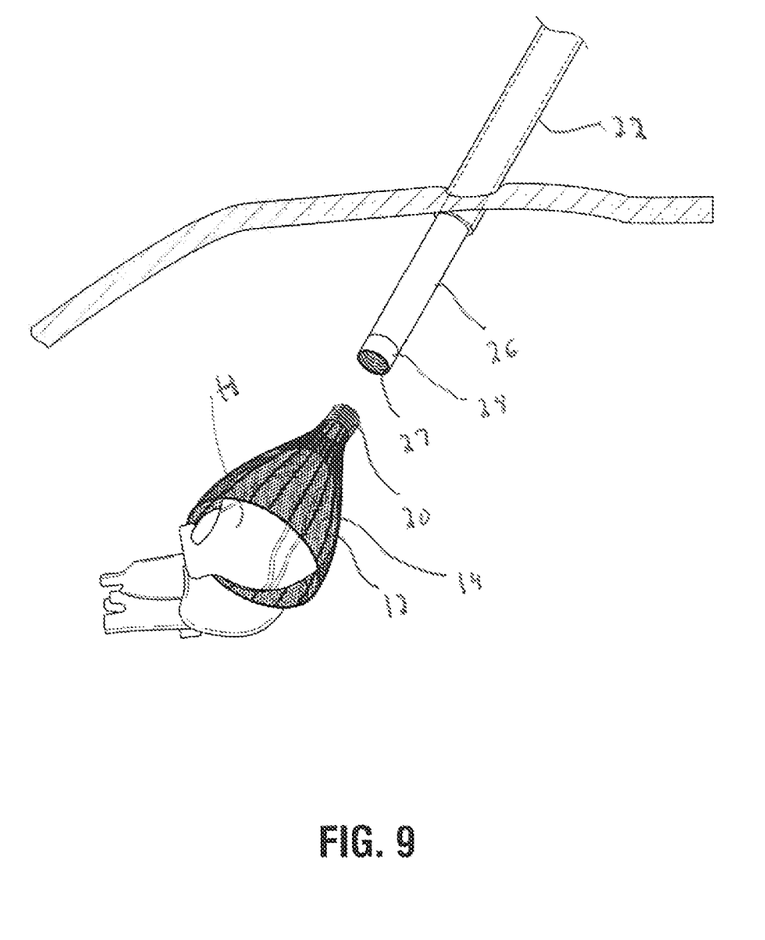
FIG. 9 illustrates the device of FIG. 1A encircling the heart and the delivery tube attached from the device and being withdrawn from the body.

A delivery sheath (such as a trocar), designated by reference numeral 24, is shown inserted through the side of the patient between the thoracic vertebrae (beneath the left breast bone and under the pectoral muscle (e.g., in the region where fluid is drained from the heart). In the preferred embodiment, it is inserted between T4 and T5 as shown in FIG. 5. After insertion of the delivery sheath 24 through the intercostal space, the insertion sheath 22 which contains therein the delivery tube 26 and the attached device 10 in the collapsed condition is inserted through the delivery sheath 24 to a position adjacent the heart H as shown in FIG. 6. The device 10 is then exposed from the insertion sheath 22 by retraction of the insertion sheath 22 and/or further advancement of the delivery tube 26 from the insertion sheath 22 so the device 10 is free from the confines of the insertion sheath 22 and the frame 12 (elongated members 15) can expand to the position of FIG. 7. With the frame open, opening 16 is advanced over the heart as shown in FIG. 7 so the heart is encapsulated within the space formed in the construct 14/elongated members 15. The retention members 19 engage (penetrate the cardiac tissue in the embodiments where they have sharpened tips) to retain the securement of frame 12 to cardiac tissue so that the construct 14 remains in contact with the heart H. Once placed over the heart, the delivery tube 26 is detached from the device 10, e.g., by rotating it (FIG. 8) to unscrew it from the threaded tube 20 of the device 10 as in the illustrated embodiment, leaving the frame 10 and attached construct 14 of contractile cells around the heart as illustrated in FIG. 9 to treat chronic heart failure or other heart conditions. After placement around (encircling) the heart, the delivery tube 26 and delivery sheath 22 are removed through the intercostal space. The construct 14 remains attached to the epicardium and allows cells to attach to it and allows cells to grow into more than one layer, thereby, as stated above, providing cell-based therapy using the heart as its own bioreactor to support the engraftment/growth of cells seeded on the 3DFCS.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A method for minimally invasively treating chronic heart failure comprising:
providing a device having a frame having a plurality of longitudinally extending elongated members and cardiac tissue attached to the frame;
inserting the device minimally invasively through a delivery member extending between T4 and T5 vertebrae of a patient;
exposing the device from the delivery member so the longitudinally extending elongated members of the device automatically expand to diverge;

placing the device around the heart to treat chronic heart failure;

minimally invasively detaching the device from an elongated delivery element after placement of the device around the heart; and removing the delivery member and delivery element through a space between thoracic T4 and T5 vertebrae of the patient.

2. The method of claim 1, wherein the frame has a plurality of tines with penetrating tips which engage the heart to retain the device around the heart, the plurality of tines spaced apart longitudinally along a length of the elongated members.

3. The method of claim 1, wherein the frame is composed of shape memory metal.

4. The method of claim 1, wherein the frame has a plurality of tines which are configured to engage cardiac tissue to retain the frame around the heart.

5. The method of claim 1, wherein the elongated members of the frame are composed of a plurality of wires.

6. The method of claim 1, wherein the elongated members of the frame are composed of a plurality of struts.

7. The method of claim 1, wherein the elongated members extend outwardly from a converging region, wherein the converging region includes a connection structure for releasable connection to the delivery element.

8. The method of claim 7, wherein the connection structure comprises a threaded engagement with the delivery element.

9. The method of claim 1, wherein the elongated members terminate in blunt atraumatic ends.

10. The method of claim 1, wherein the elongated members are attached at proximal ends via threaded engagement to the delivery element, and the delivery element is rotatable to detach the delivery element from the frame.

* * * * *